(12) United States Patent
Rodriguez Y Baena et al.

(10) Patent No.: US 9,398,841 B2
(45) Date of Patent: Jul. 26, 2016

(54) STEERABLE PROBES

(75) Inventors: Ferdinando Marie Rodriguez Y Baena, London (GB); Luca Frasson, Saronno (IT)

(73) Assignee: Imperial Innovations Limited, London (GB)

( * ) Notice: Subject to any disclaimer, the term of this patent is extended or adjusted under 35 U.S.C. 154(b) by 610 days.

(21) Appl. No.: 13/512,630

(22) PCT Filed: Nov. 30, 2010

(86) PCT No.: PCT/GB2010/051987
§ 371 (c)(1),
(2), (4) Date: Jul. 25, 2012

(87) PCT Pub. No.: WO2011/064602
PCT Pub. Date: Jun. 3, 2011

(65) Prior Publication Data
US 2012/0279325 A1    Nov. 8, 2012

(30) Foreign Application Priority Data
Nov. 30, 2009   (GB) .................................. 0920938.8

(51) Int. Cl.
| A61B 1/01 | (2006.01) |
| A61M 25/01 | (2006.01) |
| A61B 1/00 | (2006.01) |
| A61B 1/005 | (2006.01) |
| A61M 25/00 | (2006.01) |

(52) U.S. Cl.
CPC ................ *A61B 1/01* (2013.01); *A61B 1/0016* (2013.01); *A61B 1/0051* (2013.01); *A61B 1/00071* (2013.01); *A61M 25/0113* (2013.01); *A61M 25/0141* (2013.01); *A61M 25/0147* (2013.01); *A61M 25/0152* (2013.01); *A61M 25/0069* (2013.01)

(58) Field of Classification Search
USPC .......... 600/106, 128, 141, 145, 146; 73/866.5
See application file for complete search history.

(56) References Cited

U.S. PATENT DOCUMENTS

| 5,345,937 | A  | * | 9/1994  | Middleman et al. .......... 600/434 |
| 5,607,435 | A  | * | 3/1997  | Sachdeva et al. .............. 606/139 |
| 6,432,044 | B1 | * | 8/2002  | Lunsford et al. .............. 600/129 |
| 6,837,846 | B2 |   | 1/2005  | Jaffe et al. |
| 6,887,195 | B1 | * | 5/2005  | Pilvisto ......................... 600/146 |
| 6,960,164 | B2 | * | 11/2005 | O'Heeron ..................... 600/114 |
| 7,445,596 | B2 | * | 11/2008 | Kucklick et al. .............. 600/114 |
| 7,500,947 | B2 | * | 3/2009  | Kucklick et al. .............. 600/114 |
| 8,343,035 | B2 | * | 1/2013  | To ................................. 600/109 |

(Continued)

FOREIGN PATENT DOCUMENTS

| CN | 2708925 Y | 7/2005 |
| CN | 1649537 A | 8/2005 |

(Continued)

*Primary Examiner* — Peter Macchiarolo
*Assistant Examiner* — Alexander Mercado
(74) *Attorney, Agent, or Firm* — Fraser Clemens Martin & Miller LLC; William J. Clemens

(57) ABSTRACT

A steerable probe comprises a body and drive means arranged to drive the probe through a sample. The body comprises at least three body sections extending parallel to each other along the probe and each movable relative to the others along the probe. The drive means is arranged to move each of the body sections in turn relative to the others thereby to drive the probe through the sample.

20 Claims, 8 Drawing Sheets

(56) References Cited

U.S. PATENT DOCUMENTS

| | | | |
|---|---|---|---|
| 8,365,633 B2 * | 2/2013 | Simaan et al. | 74/490.04 |
| 8,439,830 B2 * | 5/2013 | McKinley et al. | 600/173 |
| 8,821,388 B2 * | 9/2014 | Naito et al. | 600/141 |
| 2003/0149338 A1 * | 8/2003 | Francois et al. | 600/152 |
| 2005/0085693 A1 * | 4/2005 | Belson et al. | 600/146 |
| 2005/0107737 A1 * | 5/2005 | McDaniel | 604/95.04 |
| 2005/0197536 A1 * | 9/2005 | Banik et al. | 600/179 |
| 2006/0178560 A1 * | 8/2006 | Saadat et al. | 600/114 |
| 2010/0261964 A1 * | 10/2010 | Danitz et al. | 600/141 |

FOREIGN PATENT DOCUMENTS

| | | |
|---|---|---|
| WO | 00/54653 A1 | 9/2000 |
| WO | 03/028224 A2 | 4/2003 |
| WO | 2008/079835 A1 | 7/2008 |
| WO | 2008/101080 A1 | 8/2008 |

* cited by examiner

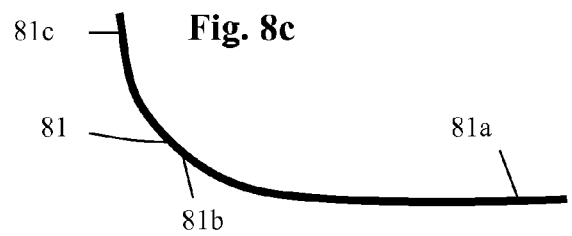
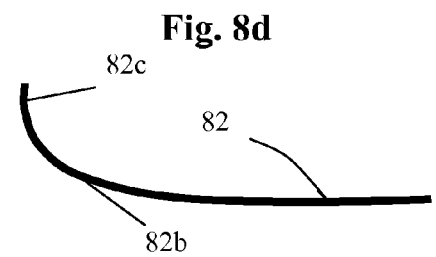
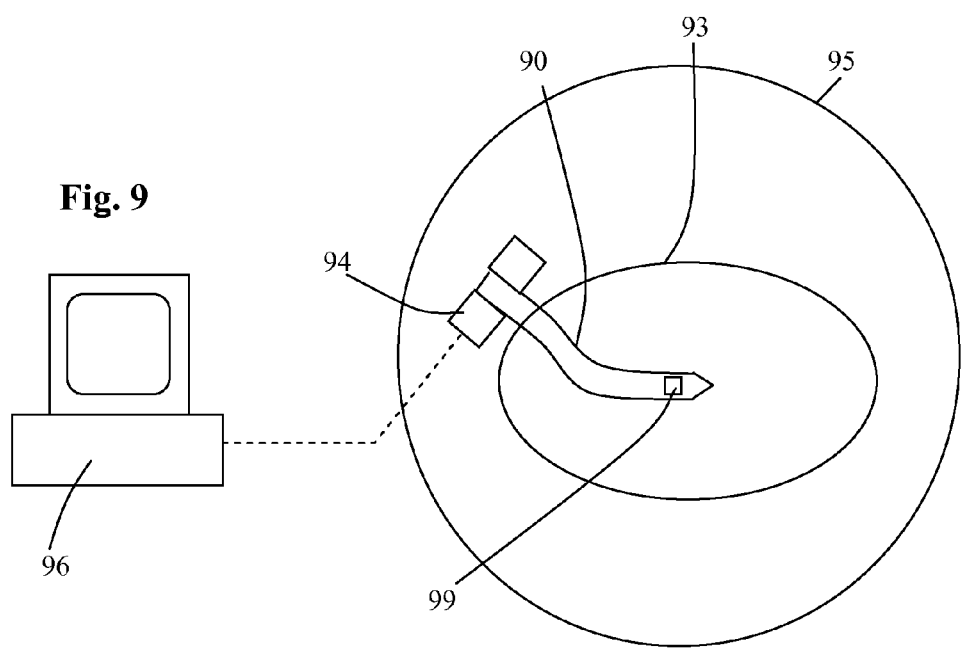
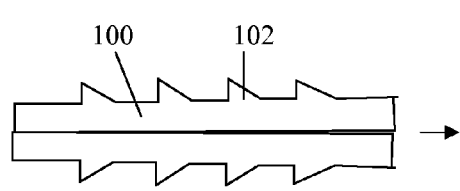
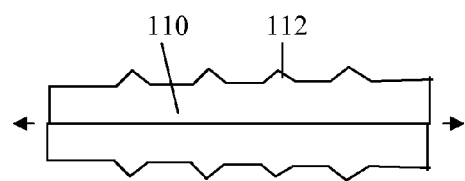

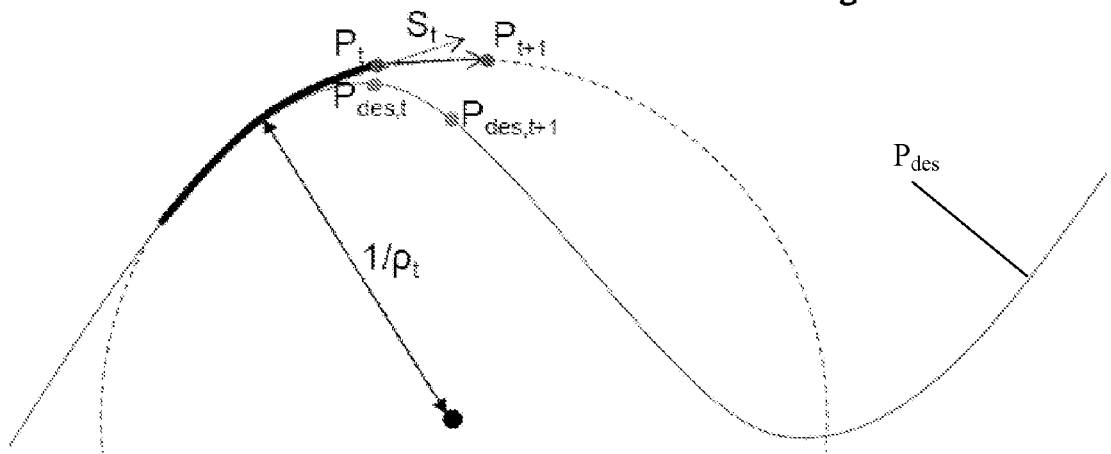
Fig. 15
Fig. 16a
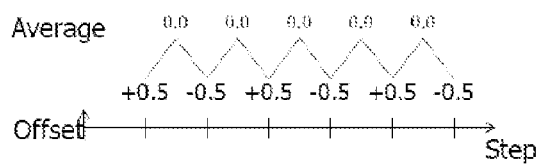
Fig. 17a
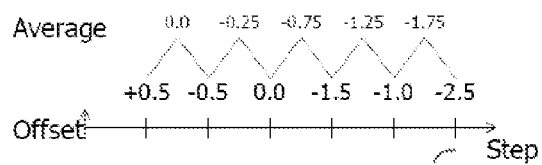
Fig. 16b
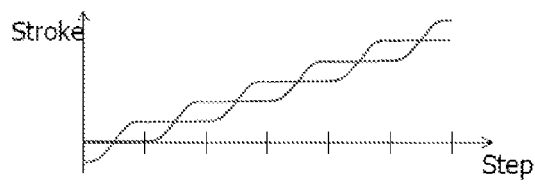
Fig. 17b
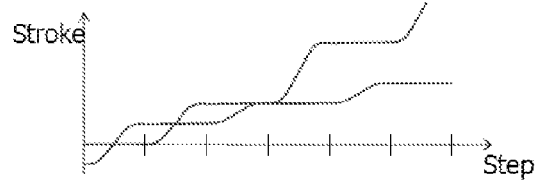

US 9,398,841 B2

STEERABLE PROBES

FIELD OF THE INVENTION

The present invention relates to steerable probes. It has application in the field of medicine, for example in surgery on the brain or liver but, unusually, it also has application in other fields such as mining and exploration.

BACKGROUND TO THE INVENTION

The current trend in medical intervention favours a less invasive approach with a tendency towards localised therapy. Surgical probes for minimally invasive (MI) access can be broadly categorised into two main groups: endoluminal and percutaneous probes. Endoluminal probes (such as endoscopes and endovascular catheters) exploit natural orifices and accessible vessels within the body to direct a tool (e.g. optical fibre, tissue sampler, etc.) to the target. Their use has proved very successful in a few key specialties, such as in gastrointestinal surgery, but the range of application areas for endoluminal access is limited. Conversely, percutaneous (i.e. through the skin) instruments are widely used across the full spectrum of "invasive intervention", as they are highly versatile with regard to the entry point and access route to a chosen soft tissue target. Current procedures which involve percutaneous insertion of needles and catheters range from blood/fluid sampling, tissue biopsy, catheter insertion, ablation and brachytherapy to deep brain stimulation and diagnostic imaging, with new approaches appearing in the literature at an ever increasing rate.

Current percutaneous instruments can be classified into two main groups: thick and non-flexible probes (e.g. biopsy probe and laparoscopes) and thin and flexible needles (e.g. a brachytherapy needle). Thick and non-flexible probes have the advantage that they can be pointed to the target with the aid of a visualisation system (e.g. ultrasound) and will not deform under load. Their manipulation, however, causes significant pressure on the tissue, which limits the surgeon's degrees of freedom. Conversely, thin and flexible probes tend to be less damaging to the surrounding tissue, but deflect and buckle against tissue resistance, resulting in placement accuracy which is inversely proportional to the depth of the target. Additionally, both groups suffer from the same underlying technological and functional limitation: they cannot be guided along curvilinear trajectories. This is a fundamental drawback of percutaneous probes, which limits their application to surgical procedures where a straight line approach is viable.

Three main research lines have previously been followed to solve the needle steering problem. Recent studies have shown that, as a flexible needle with a bevel tip is pushed through soft tissue, the asymmetry of the tip itself causes the needle to bend along a curved trajectory with a single radius. There has also been demonstrated a control strategy to alter the trajectory of the bevel tip during insertion; proportional control of the curvature of the trajectory can be achieved via duty-cycled spinning of the needle itself, where the approach angle of the needle can be controlled through a cyclical rotation along the longitudinal axis. The main shortcoming of the bevelled-tip approach to needle steering, however, pertains to limitations in the cross-sectional diameter of the needle, which is inherent to the steering mechanism itself. Since trajectory control is achieved through duty cycling, the material which the needle is made of needs to be sufficiently stiff to enable the transmission of a torque along the entire length of the needle (which explains the choice of a nitinol stranded wire), while the diameter should be small enough for the needle to be flexible and thus able to bend (currently 0.28 mm). Given the contrasting requirements of a stiff structure and a highly flexible needle, such limitation on the maximum outer diameter cannot be exceeded.

In an alternative approach to needle steering a standard needle is steered along a curved trajectory inside soft tissue (e.g. turkey breast muscle) by applying a moment at its base. The insertion trajectory is planned by modelling tissue and needle interaction and deformation using a simplified spring-damper approach. However, since the targeting performance relies upon tissue stiffness and resistance, the range of applicable soft materials where such control strategy can be used is limited. The application of this approach on soft and delicate tissues such as brain would result in severe tissue tear.

The third and final approach to needle steering is based on combining pre-curved concentric tubes, which can be rotated and extended with respect to each other to control the tip position and orientation. While this approach poses a relatively simple control problem, as the tube segments and their interaction can be modelled using simple beam theory, the range of available trajectories achievable with any one needle embodiment is highly limited. Since each pre-curved tube has a "fixed" geometry and radius of curvature, a trajectory with controlled variable curvature is impossible by design. In addition, the number of curves in the path is irreversibly tied to the number of segments (e.g. three concentric tubes can only produce a curved path with two constant radius curves), which limits the range of applications for which the probe would be suitable.

In summary, while these research efforts have substantially advanced the state of the art, all solutions proposed to date have limited application scope. Hence, there still exists a clear need for new, versatile technology that will enable percutaneous interventions in the body to be executed with accuracy and with minimum disruption to the surrounding tissues: a thin and flexible working channel which can be accurately positioned anywhere within the body, for application to a variety of surgical applications.

SUMMARY OF THE INVENTION

The present invention provides a steerable probe comprising a body and drive means arranged to drive the probe through a sample. The body may comprise at least three body sections extending parallel to each other along the probe and each movable relative to the others along the probe. It has been found that, with at least three body sections, when one of the sections is moved, the others tend to remain substantially still. This is because when two unequal parts of the surface of the probe are moved relative to each other, the larger surface tends to remain still and the smaller surface tends to move relative to the sample in which the probe is located. The drive means may be arranged to move each of the body sections in turn, for example one at a time or in groups, in a sequence which may be variable, relative to the others thereby to drive the probe through the sample.

The drive means may be arranged, when applying a force in a forward direction to one of the body sections, to apply a force in a rearward direction on at least one of the other body sections. This can reduce or limit the total or net external force applied to the probe. The drive means may be arranged to balance the forces that it applies to the body sections in the forward and rearward directions so that it applies substantially zero net force to the probe.

The drive means may be arranged to act between the body sections so as to apply forces that are internal to the probe.

Alternatively the drive means may be arranged to apply forces between the body sections and another body, which may be fixed, or may be arranged to move with the probe through the sample.

One or more of the body sections may comprise steering means arranged to steer it in a respective direction if it is moved forwards of the other body sections. This steering means may comprise a shaped tip, or resilient biasing means, or both. The resilient biasing means may be in the form of a resilient insert in the body section, or it may comprises a portion of the body section itself which is formed of a resilient material, for example by injection moulding. The steering means may be passive or active.

Each of the body sections may have an outer surface which forms part of the outer surface of the probe, the outer surface having a texture. The texture may be arranged to resist movement through the sample equally in both longitudinal directions of the probe. Alternatively it may be arranged to resist movement in one direction more than in the other.

The drive means may comprise actuation means arranged to apply drive forces to the body sections and control means arranged to control the actuation means so as to control movement of the probe. The actuation means may be mounted on the probe body and arranged to move with the probe body through the sample. Alternatively the actuation means may be located remote from the probe and connected to the probe by force transmission means, thereby allowing the actuation means to be located outside a volume in which electrical components are undesirable, such as an MRI scanner.

The probe may have a channel extending through it, for example for the passage of tools or medicines along the probe, or for the extraction of samples or cores of the sample. The channel may extend through one of the probe sections, or may be defined between two of the sections, or centrally between all of the sections.

The present invention further provides a probe system comprising a probe according to the invention and locating means arranged to locate the probe as it moves though the sample. The drive means of the probe may be arranged to receive location signals from the location means so as to provide closed loop control of the position of the probe.

The probe may be a medical probe. The probe is preferably MRI compatible. Unusually the probe may have applications outside the medical field and may be arranged for geological use, or for search and rescue uses, for example in snow.

The present invention further provides a probe according to the invention and further comprising detection means, wherein the drive means is arranged to determine a desired direction from the detection means and to control the movement of the body sections so as to move the probe towards the desired direction.

Preferred embodiments of the present invention will now be described by way of example only with reference to the accompanying drawings.

BRIEF DESCRIPTION OF THE DRAWINGS

FIGS. 8c and 8d show steering members which can be used in the probe of FIG. 8a;

FIG. 9 is a schematic diagram of a surgical system including a probe according to an embodiment of the invention;

FIG. 10 is a section through part of a probe according to a further embodiment of the invention;

FIG. 11 is a section through part of a probe according to a further embodiment of the invention;

FIG. 15 is a diagram showing the geometry of the controller path of the probe in the system of FIG. 12;

FIGS. 16a and 16b are graphs of offset and stroke position of the sections of the probe of FIG. 12 with constant offset;

FIGS. 17a and 17b are graphs of offset and stroke position of the sections of the probe of FIG. 12 with varying offset;

DESCRIPTION OF THE PREFERRED EMBODIMENTS

Figure 1:
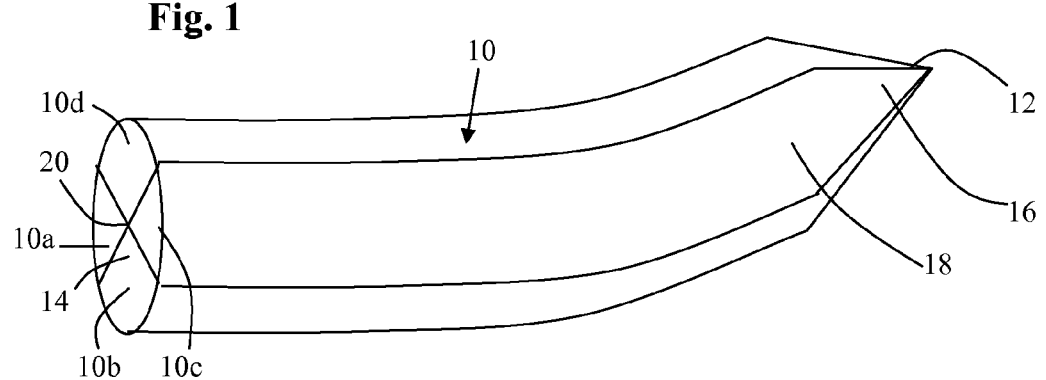
FIG. 1 is a schematic view of a probe according to an embodiment of the invention.

Referring to FIG. 1, a steerable probe for use in brain surgery comprises an elongate flexible body 10 formed of four body sections 10a, 10b, 10c, 10d each of which extends the full length of the body 10 from its front end 12 to its rear end 14. The body 10 is of a circular cross section, and each of the four body sections 10a 10b, 10c, 10d has a cross section which is generally in the form of a segment, in this case a quarter, of the overall circular cross section. The front end 12 of the probe is tapered to a point so each of the body sections has a tapered or bevelled tip 16 at its front end, where its outer surface 18 tapers inwards towards the longitudinal centre line 20 of the probe. The body sections 10a 10b, 10c, 10d are connected to each other by means of interlocking formations, described in more detail below, which allow the body sections to slide backwards and forwards relative to each other. The probe is shown as being quite short for the sake of clarity, but in practice a probe for this type of surgical application would generally be around 1.5 to 10 mm in diameter and about 100 to 300 mm in length.

Figure 2A:
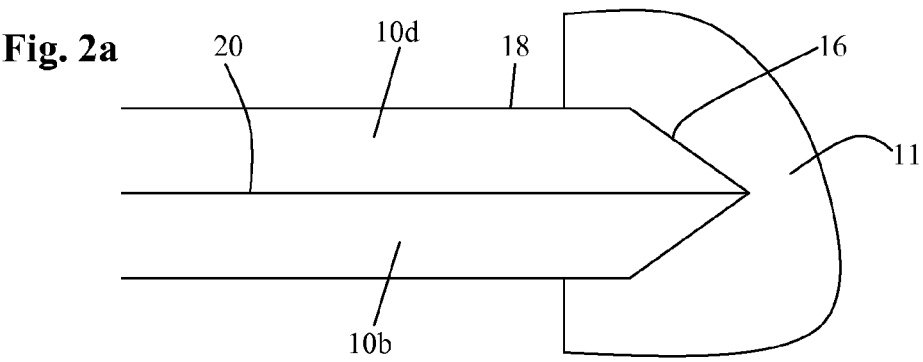
FIGS. 2a, 2b and 2c are longitudinal sections through the probe of FIG. 1 in different stages of operation.
Figure 2B:
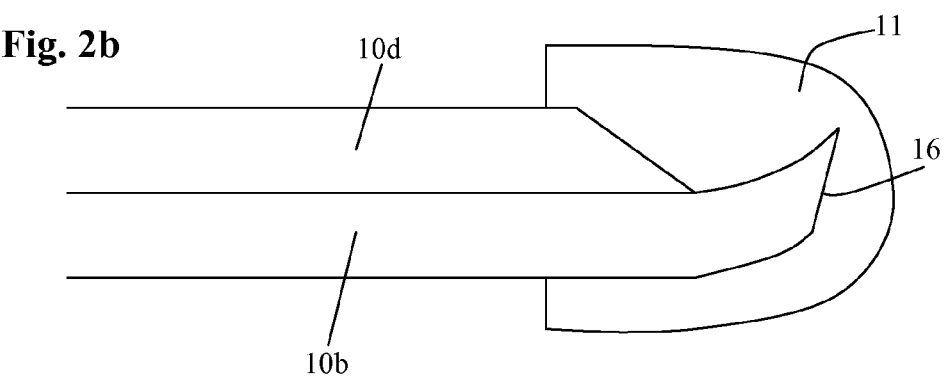
Figure 2C:
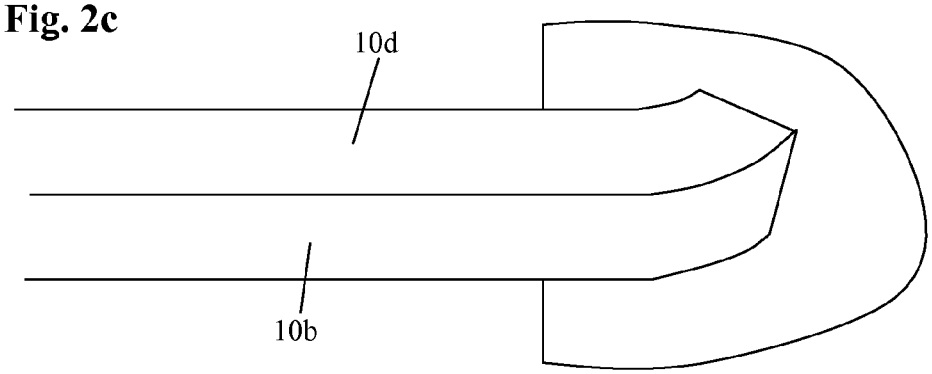

Referring to FIGS. 2a to 2c, the probe is moved into a sample 11, in this case the brain, by moving the body sections forwards in turn, one at a time. The order in which the body sections are moved controls the steering of the probe. If one of the body sections 10b is moved forwards ahead of the others, its bevelled tip 16 tends to cause it to bend inwards as shown in FIG. 2b. When the opposite body section 10d is moved forwards to be level with the first one 10b then it tends to follow the curved path formed by the first body section 10b as shown in FIG. 2c. The other two body sections 10a, 10c will also tend to follow the first one 10b when they are moved forwards to be level with it, although they may add a small component to the curvature in the direction away from the first of them to be moved. Therefore the probe can be advanced along a curved path, the direction of which is determined by, among other things, the order in which the body sections 10a 10b, 10c, 10d are advanced.

Figure 3:
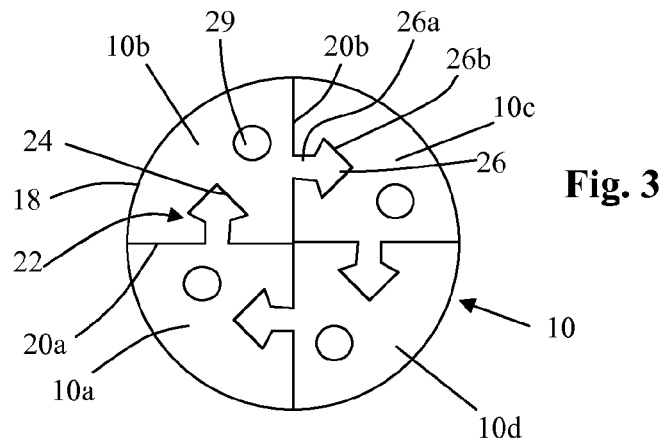
FIG. 3 is a cross section through the probe of FIG. 1.

Referring to FIG. 3, in this embodiment each of the four body sections 10a 10b, 10c, 10d is of constant cross section over most of its length and can therefore conveniently be formed from an extrusion of elastomeric material. All four body sections 10a 10b, 10c, 10d are the same, each having a curved outer surface 18 and two inner surfaces 20a, 20b arranged to be in sliding contact with the corresponding surfaces on the two adjacent body sections. As the body sections are all similar, the curved outer surface of each is substantially the same size, and therefore in this case forms one quarter of the outer surface of the probe. The interlocking formations 22 are in the form of an undercut groove 24 formed in one of the flat inner surfaces 20a and a correspondingly shaped rib 26 projecting from the other of the flat inner surfaces 20b. The rib 26 has a narrow neck 26a at its base and a wider top portion 26b so that it fits into the groove 24 in the adjacent body section and interlocks with it to prevent the two adjacent body sections 10a 10b, 10c, 10d from coming apart. However, the constant cross section of the body sections 10a 10b, 10c, 10d means that they can slide relative to each other along the length of the probe, as described above. Each section also has a bore or channel 29 extending along it which can be used to pass surgical instruments along when the probe is inserted in the sample, such as minimally invasive tools, which may be passive or active and could include catheters or biopsy needles.

Figure 4:
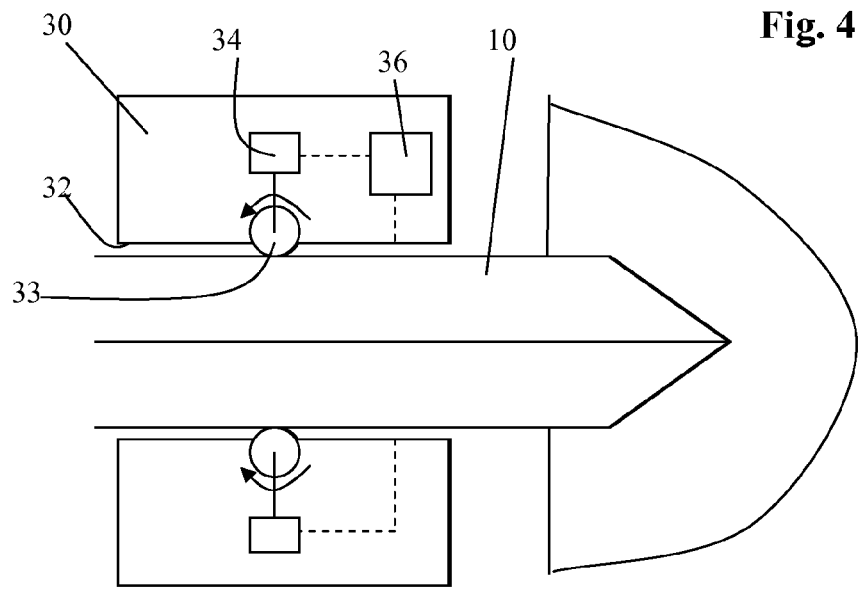
FIG. 4 shows a drive mechanism for a probe according to an embodiment of the invention.

Referring to FIG. 4 a drive mechanism for the probe of FIGS. 1 to 3, shown very schematically and not to scale, comprises a support housing or guide 30 with an aperture 32 through it through which the probe body 10 can be fed. Four drive rollers 33 are spaced around the inner wall of the aperture so that each of them can make rolling contact with a respective one of the probe body sections 10a, 10b, 10c, 10d. Each of the drive rollers 33 is independently driven by a respective drive motor 34, all of the drive motors 34 being controlled by a control unit 36. The drive motors 34 are bi-directional so that each of the probe body sections 10a, 10b, 10c, 10d can be moved forwards or backwards independently of the others. The control unit 36 is arranged to control the drive motors 34 so as to control the force applied to each of the probe body sections 10a, 10b, 10c, 10d, thereby to control the movement of each of the body sections 10a, 10b, 10c, 10d.

The control of forces on the probe sections 10a, 10b, 10c, 10d can be performed in a number of ways. As described above, the movement of each body section 10a, 10b, 10c, 10d will generally be in steps, with each step comprising a forward movement of one of the probe sections relative to the others. In one mode of operation, for each step, the distance moved by each of the body sections is controlled. Specifically all of the sections 10a, 10b, 10c, 10d apart from one are held stationary, while that one section is moved forwards by a predetermined distance. At each step a different section is moved from the previous step, and in this way the sections are moved forward in turn. This results in the sections being moved in a series of cycles, each of which comprises a forward step of each of the sections 10a, 10b, 10c, 10d. Each cycle may begin when all of the sections are level and ends when they are again all level, i.e. with no fixed offset between the sections. Alternatively, if the probe is turning with a fixed curvature, there may be a fixed offset between the sections, as will be described in more detail below. In this case the sections will not be level, but will be in the same positions relative to each other at the beginning and end of the cycle. In other cases, where the turning curvature is changing, the cycle may include an overall change in the relative positions of the sections.

It will be appreciated that, in the movement-based control described above, the net longitudinal force on the probe will vary. In general, the total rearwards force applied to the stationary body sections to keep them stationary will not be equal to the forward force applied to the moving body section. In a different mode of operation the motors 34 are controlled so as to control the forces applied to the body sections 10a, 10b, 10c, 10d. At each step, the forces are applied until the forward moving section has moved a predetermined distance relative to the other sections, but the balance between the forward force on the forward moving section and the rearward force on the other sections is controlled so as to control the net (i.e. total) force on the probe. For example, the net force can be set to be zero, in which case the forward force on the forward moving section will be equal to the total rearward force on the other sections. This has the advantage that there is no net push on the probe which might tend to cause buckling of the probe and also no net pull on the probe, which might tend to cause straightening of the probe. Either of these can cause damage to the tissue through which the probe is moving. However in some cases movement through the sample may require a controlled net forward force, in which case the forward force on the forward moving section can be controlled so as to be greater than the total rearward force on the other sections.

In order that the probe can be moved back out of the sample, the direction of movement, and the forces applied, can be reversed, so that each of the body sections 10a, 10b, 10c, 10d is stepped backwards in turn as for forward movement. In this case a controlled net pulling force can also be applied to the probe if required.

In this embodiment the control unit 36 is arranged such that the total net force is variable and can be set by a user. The relative movement for each step is also variable and can be set by a user, as can the direction of movement.

Figure 5:
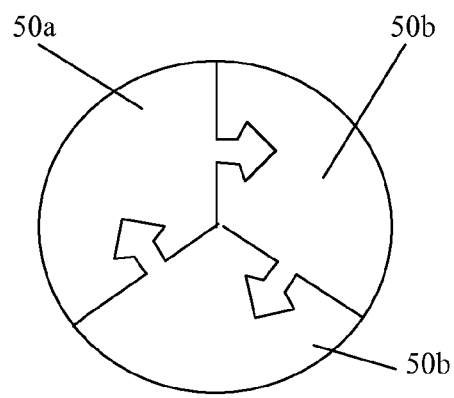
FIG. 5 is a cross section through a probe according to a further embodiment of the invention.

It will be appreciated that the number of sections into which the body is divided can vary depending on the application. The use of four sections has the advantage that control of the curved path of the probe is relatively easy to control as the two pairs of opposite sections can be used to cause curvature in two orthogonal planes. However, referring to FIG. 5, a probe made of three sections 50a, 50b, 50c can be used, and can be controlled to move in a three dimensional curved path with suitable ordering of the movement of the sections 50a, 50b, 50c. In this case, as the curved outer surfaces of the sections are equal in size, each makes up a third of the outer surface of the probe. Similarly probes of more than four sections can be used. In each case, for the probe to move while no net external force is applied to it, the surface area of the moving section, or sections, at any time needs to be less than that of the stationary sections. Clearly the higher the number of sections, and therefore the smaller the proportion of the surface area is moved at once, the more likely it is that the 'stationary' sections will remain truly stationary while the other section moves. However, provided the moving surface area is greater than the 'stationary' surface area then, with appropriate surface texture on the probe, it will generally be possible for 'stiction' effects to be used to keep the 'stationary' sections truly stationary while the 'moving' section moves relative to the sample. Even if the 'stationary' sections in fact move in the opposite direction than the 'moving' section, this will generally be only by a small amount so that, over the course of a cycle of movement, the probe as a whole will move in one direction.

Clearly, body sections of unequal size can be used, for example where some of the sections are primarily steering sections and others are non-steering sections, the two groups of sections can be of different sizes or of different shapes, or both.

Figure 6:
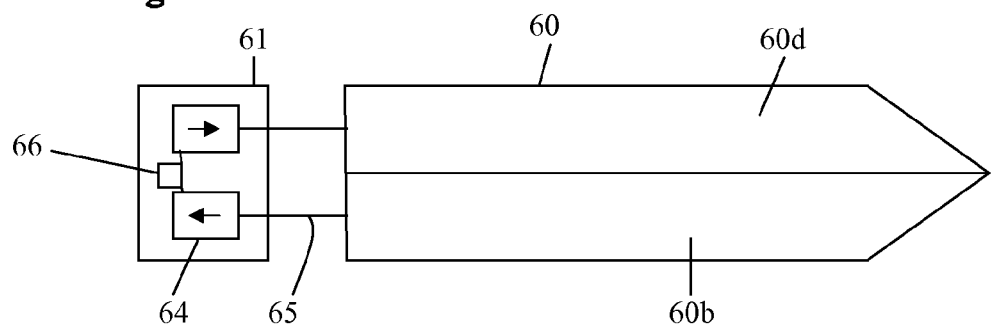
FIG. 6 is a schematic longitudinal section through a probe according to a further embodiment of the invention.

Referring to FIG. 6, a probe according to a further embodiment of the invention comprises four body sections, only two of which 60b, 60d are shown in section, of the same general form as those of FIG. 3. In this case the drive mechanism is arranged to move with the probe body 60. The drive mechanism comprises a housing 61 with four actuators 64 mounted in it, each of which is connected via a push rod 65 to the rear end of one of the body sections 60b, 60d. Each of the actuators is therefore arranged to move a respective one of the probe body sections 60b, 60d forwards or backwards relative to the drive mechanism housing 61. The drive mechanism can therefore move the individual body sections 60b, 60d forwards or backwards by a controlled distance in turn as with the embodiment of FIG. 4. However the net force applied by the actuators 64 on the probe (including the drive mechanism) will be zero as the forces applied are all internal to the probe. Therefore no net forward or backward force can be applied to the probe by the actuators 64, and the movement of the probe will depend on the interaction between the outer surface of the probe and the sample through which it is moved.

The actuators are controlled by a control unit 66 which is also mounted in the drive mechanism housing 61. The control unit is arranged to control the actuators 64 so as to move each of the probe body sections 60b, 60d forwards relative to the others in turn. However in this case, when all of the body sections 60b, 60d have been moved forwards by one step relative to the drive mechanism housing 61 by means of the actuators 64 pushing forwards on the respective push rods 65, the actuator housing 61 is then moved forwards by one step at the end of the cycle by the actuators pulling simultaneously on all of the push rods 65, before the next cycle begins with the first body section moving forwards. This pulls the drive mechanism housing 61 forwards towards the probe body 60.

Figure 7:
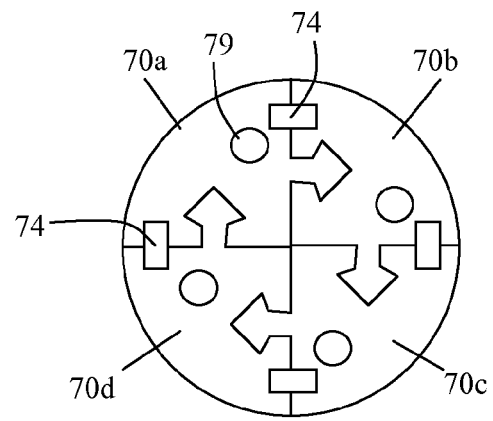
FIG. 7 is a schematic cross section through a probe according to a further embodiment of the invention.

Referring to FIG. 7 a probe according to a further embodiment of the invention again comprises four probe body sections 70a, 70b, 70c, 70d slidable longitudinally relative to each other. In this case each of the four actuators 74 acts directly between a respective pair of adjacent body sections so that it can move each one of the pair in either direction, forwards or backwards, relative to the other. Therefore by coordinated operation of the four actuators 74, each one of the body sections can be moved forward in turn, relative to the others, as described above. The actuators are piezoelectric actuators which can be MRI compatible and housed entirely inside the body. This allows the probe to have a pointed tip at both ends and the controller for the actuators is arranged so that, at each step, the one body section that moves relative to the others can move in either direction. This means that the probe can move in either direction through the sample. Another advantage of this type of actuation mechanism is that it can be located anywhere along the length of the probe. For example the actuators can be located near the front end of the probe with power supplied to them along channels 79 through the probe. This means that the movement of the tips of the body sections can be controlled more accurately than if the actuators act at the rear end of the probe, in which case the movement has to be transmitted along the full length of the probe. In some embodiments two or more sets of actuators are placed at different locations along the probe. Alternatively with this type of actuator, the probe can be made significantly shorter, for example being a few centimeters long, which means that the transmission of forces along the probe is not a significant issue.

Figure 8A:
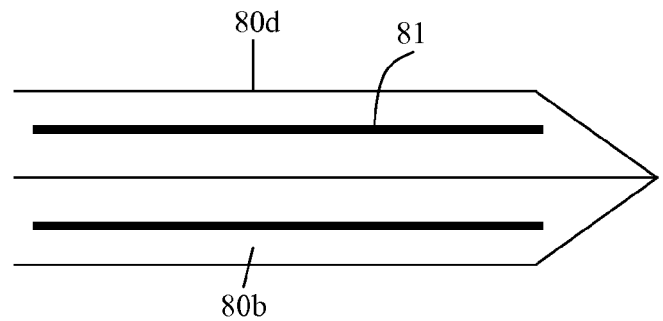
FIGS. 8a and 8b are longitudinal sections through a probe according to a further embodiment of the invention in different stages of operation.
Figure 8B:
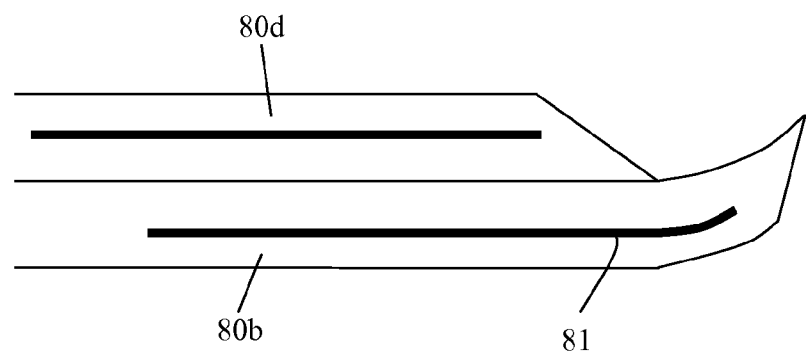

Referring to FIGS. 8a and 8b, in a further embodiment each of the body sections 80b, 80d has a resilient steering member 81 extending along it parallel to the central axis of the probe. Each steering member 81 is, in its relaxed state, curved, as shown in FIG. 8c. However the steering members of each pair of body sections 80b, 80d on opposite sides of the probe are curved in opposite directions so that, when all the body sections are level with each other in the longitudinal direction, as shown in FIG. 8a, the internal forces in the probe produced by the steering members 81 tending to resume their natural curved shapes, balance out, so that the probe remains straight. When one of the body sections 80b is moved forwards, as shown in FIG. 8b, the part of the steering member 81 in that section which projects beyond the front ends of the other sections 80d can start to resume its natural curved state. This therefore tends to steer the leading body section round a curve having the natural radius of curvature of the steering member 81. The probe shown in FIGS. 8a and 8b has a bevelled tip which adds to the steering effect, but in other embodiments there is no bevelled tip and the resilient steering members provide all the required steering. When the other non-leading body sections are moved forwards, while the bending forces of the steering members tends again to balance out, they still tend to follow the curved path of the leading body section 80b because the tissue of the sample through which the probe is moving tends to prevent the probe from simply straightening. Therefore with this steering mechanism, as with the bevelled tips steering mechanism, the direction of steering can be controlled by controlling the order in which, and the step length by which, the body sections 80b, 80d are moved forwards.

Referring to FIG. 8c each of the steering members 81 has a substantially straight portion 81a at its front end, and then a curved portion 81b of substantially constant radius of curvature at its rear end 81c. Referring to FIG. 8d, in a further embodiment, the curved front portion 82b of the steering members has a radius of curvature which varies along its length, in this case getting smaller towards its rear end 82c. It will be appreciated that the shape of the steering member in its relaxed state can be selected to determine the steering angle of the probe.

In a further modification to these embodiments, rather than passive resilient steering inserts, the steering members can be active, for example being of piezoelectric material, so that their curvature can be varied under the control of a curvature control signal. The control signal will typically be in the form of an electric voltage applied via suitable connecting wires which can extend along channels in the probe body sections. In this case the controller 36, 66 is arranged to control the degree of curvature of the steering members as well as the other parameters of the probe so as to achieve the desired path.

In a further modification the tips of the probe body sections are formed so as to have a stiffness, in particular a Young's modulus, which varies along the length of the probe tips. This can be achieved by forming the tips as a composite of a number of different materials. Specifically the stiffness of the tips is arranged to decrease towards the front ends of the tips. This results in a steering curve that varies with the amount of offset between the leading and trailing body sections as with the device of FIG. 8d.

In a still further modification the tips of the probe body sections are detachable from the main length of the probe body sections. This allows a variety of different tips with different turning characteristics to be attached to the probe so that the steering characteristics can be selected to suit any particular application. In particular different tissues with different stiffnesses will require probes with different steering mechanisms, and interchangeable tips can allow this to be achieved with a single probe.

It will be appreciated that the probe of FIG. 1, and also the probe of FIGS. 8a and 8b, the radius of curvature that the leading body section will adopt, and hence the tightness of the curved path that the probe as a whole will follow, is partly dependent on the distance through which the leading body section is moved ahead of the others, i.e. the length of each step. In general the further ahead the leading body section is moved, the smaller radius of curvature it will adopt. This means that, as well as controlling the direction of curvature by controlling the order of movement of the sections, the controller can also control the radius of curvature of the path followed by controlling the length of the steps taken. In a further addition to the control strategy, each movement cycle may not begin and end with all body sections being level in the longitudinal direction. The leading body section may start slightly ahead even before the stepped movement cycle begins. This will tend to decrease the radius of curvature of the path followed. In general terms, control of the body sections will comprise defining a starting offset between the positions of the body sections, which will be constant for any desired curve radius and direction, and then superimposing on that the stepping movements for which both the order and the length can be variable and controlled as required to produce the desired curved path. The resultant steering angle will of course also depend on the shape of the resilient steering member, if one is used, and the shape of the probe tip.

In order to simplify the control it may be preferable to use only four basic turning directions, corresponding to each of the four body sections being the leading section. In that case, for each turning direction, the section opposite the leading section will generally be the last to move in each cycle. The order of movement of the remaining two sections can be alternated from each cycle to the next, so that any steering effects caused by those two sections moving at different times are cancelled out over two cycles. In more complex control strategies more than four turning directions may be used corresponding to the different possible orders in which the four body sections can be moved.

Referring to FIG. 9, a surgical system comprises a probe 90, which in this case is the same as that shown in FIG. 1 and includes a tracking device 99, which may be an electromagnetic (EM) tracking device, near its tip so that its position can be accurately monitored. The drive mechanism 94 is controlled by a computer 96 which can control the fixed offset between the sections, the step length and the order of movement of the sections, and the net pushing or pulling force applied to the probe, so as to achieve any desired path through the sample which in this case is a brain 93. The probe is arranged to be used within a scanner 95, such as an MRI scanner, and the tracking device 99 as well as the MRI image of the probe 90 can therefore both be used to monitor the position of the probe and the path it is following as it is moved through the sample. This means that a feedback control system can be used to control the direction and radius of curvature of the path of the probe to ensure that the probe follows a desired path, and that tissue deformation occurring during tissue traversal is accounted for.

As mentioned above, the movement of the probe through the sample will depend on the interaction between the probe and the material of the sample through which it is moving.

Referring to FIG. 10, in some cases the outer surface of the probe 100 can be provided with surface texturing in the form of barbs or teeth 102 which have a directionality such that the probe 100 can move more easily in one direction than in the other. This can help to move the probe through the sample, particularly where no net force is applied to the probe by the actuation mechanism. However, such directional texturing will clearly make movement of the probe in the non-preferred direction more difficult and, in medical applications, may result in damage to the sample on withdrawal of the probe. Therefore, referring to FIG. 11, in some cases the outer surface of the probe 110 is textured in a symmetrical manner, for example comprising teeth or ridges 112 which are symmetrical in the longitudinal direction, i.e. about a transverse plane through the probe. This surface texturing therefore resists movement through the sample equally in both longitudinal directions of the probe. This allows the probe to be moved equally easily in either direction through a sample, by appropriate control of the order and direction of movement of the body sections. The scale and exact shape of the texturing can be selected so as to maximise the efficiency of movement through the sample by maximising the stiction effects that are used to ensure that only the one 'moving' section moves significantly relative to the sample, while the remaining sections remain substantially stationary.

Figure 12:
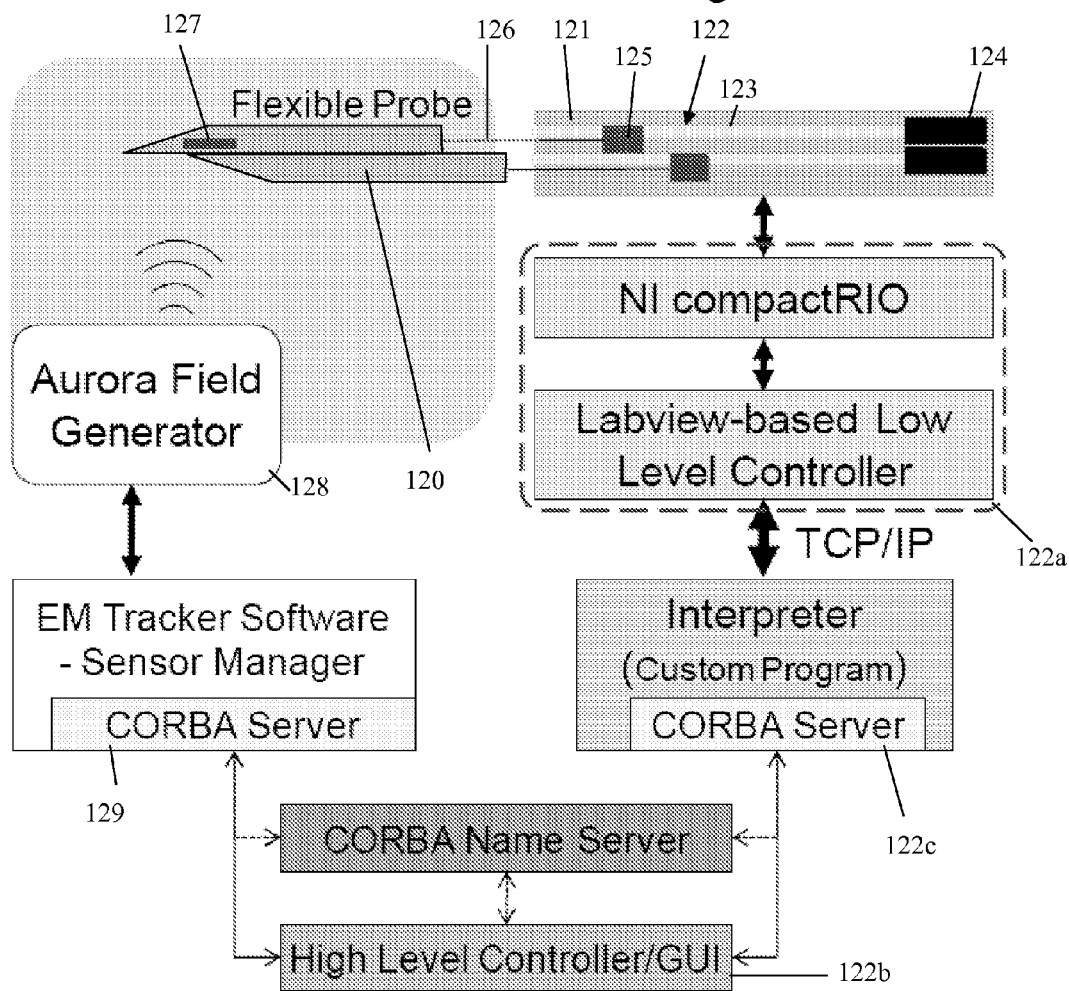
FIG. 12 is a diagram of a surgical probe system according to a further embodiment of the invention.
Figure 13:
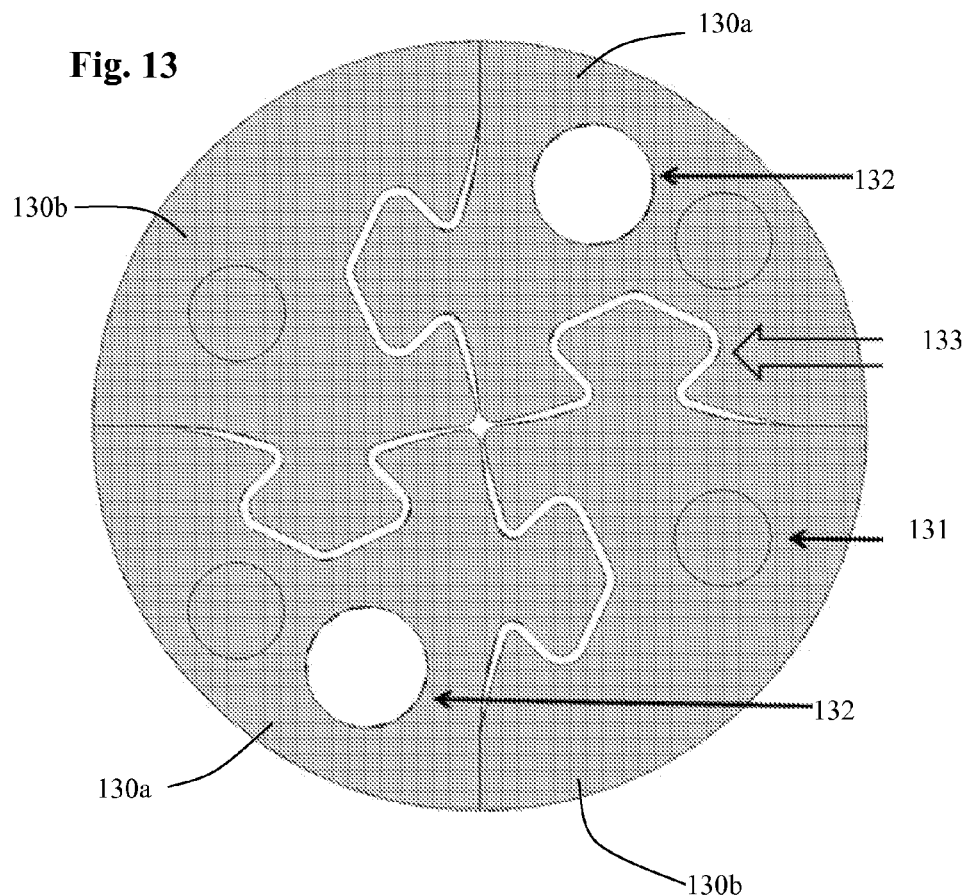
FIG. 13 is a section through the probe of the system of FIG. 12.

Referring to FIG. 12, in a surgical probe system according to a further embodiment of the invention, a probe 120 has four sections 130 which are shown in cross section in FIG. 13. The probe is driven by a fixed actuator box 121 which houses four linear actuators 122, one for each probe section 130. Each actuator comprises a drive screw 123 driven by a motor 124, and having a driven member 125 threadingly engaged with it and sliding on bearings (not shown) so that it will move linearly. Each driven member 125 is connected to a respective one of the probe sections 130 by a flexible cable or push rod 126. The probe 120 has a tracking sensor 127 mounted in its tip which forms part of a tracking system also comprising a tracking field generator 128 and a tracking controller 129 which includes tracking software and a sensor manager. The actuators 122 are controlled in operation by a low level position controller 122a. High level positioning of the probe 120 is provided by a high level controller 122b which communicates directly with the tracking controller 129 and with the low level controller 122a through an interpreter 122c.

Referring to FIG. 13, the four sections 130 the probe 120 all have the same interlocking cross sectional profile which is similar to that of the probe of FIG. 3. Each probe section 130 has a rigid portion at its rear end with a hole 131 in which the end of the flexible push rod is engaged. Two of the sections 130a, on opposite sides of the probe, have hollow channels 132 extending along their length, one of which can be used for drug delivery and the other of which can be used for connections to the tracking sensor 127. These two sections 130a have no steering insert in them, their front ends being very flexible. The other pair of probe sections 130b, which again are opposite each other, do have resilient flexible steering inserts similar to those of FIG. 8d. The shape of the interlocking features 133 is similar to those of the probe of FIG. 3.

In this embodiment the probe is 200 mm long and 12 mm in diameter. The maximum length of each movement step of each segment is 6 mm and the maximum speed of each segment is 6 mm/s. This probe length is suitable for a brain probe, though some variation in length is possible. Probes for other medical applications can be of different lengths. The diameter may be reduced, for example down to 5 or 4 mm or smaller, depending on the manufacturing process. Again, for other applications, larger diameters may be acceptable, but smaller diameters will generally be preferable provided sufficient control can be maintained.

The system can be arranged to maximise MRI compatibility. For example the length of the cables can be made sufficient for the actuators, and specifically the motors 124, to be located outside an MRI scanner volume, while the probe is being used within the scanner.

Figure 14:
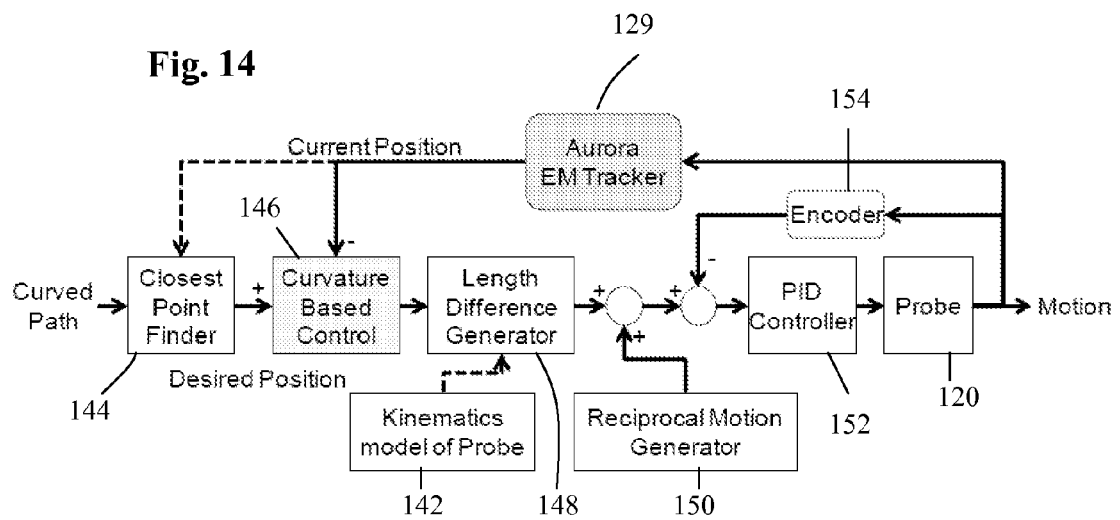
FIG. 14 is a functional diagram of the control of the system of FIG. 12.

Referring to FIG. 14, the functional units of the low level position controller 122a will now be described. The controller 122a has stored in memory a kinematic model 142 of the probe. The controller is arranged to receive data defining a desired curved path through the patient's brain. The EM tracker system 129 determines the current location of the probe 120. A closest point finder 144 determines, for each forward movement cycle, the closest point on the desired path to the current probe position and a curvature based control module 146 determines the required degree of curvature for the next forward step cycle. A length difference generator 148 and a reciprocal motion generator 150 determine the required longitudinal offset and the order and length of the movements of the individual probe sections 130 to achieve the desired curvature, based on the model 142 of the probe. A PID controller 152 drives the movement of the probe sections in the desired manner, using feedback from an encoder 154.

Referring to FIG. 15, the current curvature of the probe 120 is defined as $\rho$ where the radius of curvature at time t is $1/\rho_t$. The desired path is defined as $P_{des}$ and the positional error $\epsilon_p$ is calculated as the difference between the current position, as determined by the tracking system, and the desired position at any time t. The slope error $\epsilon_s$ is calculated as the difference between the direction (slope) in which the front end of the probe 120 is pointing, as determined by the tracking system, and the desired direction at time t. At each step cycle a target curvature $\rho$ is calculated from the errors using proportional/derivative (PD) control, using the equation: $\rho = k_\rho \epsilon_\rho + k_s \epsilon_s$ where $k_\rho$ and $k_s$ are constants. As curvature is related to the net offset between the steering sections by an approximately linear relationship, the offset required to produce the target curvature can be calculated.

Referring to FIGS. 16a and 16b, when the probe is being moved in a straight line with fixed, zero, net offset between the steering probe sections 130b, the two steering sections 130b are moved forwards alternately. Assuming a fixed step length and fixed step period, the offset will alternate, with each steering probe section 130b being 0.5 steps ahead after it has moved forwards. FIG. 16a shows the offset as a function of time, and FIG. 16b shows the position of the two sections 130b as a function of time with respective curves. Both sections 130b move in steps of the same length with the same velocity.

Referring to FIGS. 17a and 17b, if the offset is to be varied to change the steering angle, whilst maintaining the same steering direction, then provided the desired change of offset is larger than a minimum amount, this is done progressively over a number of steps. This allows the sequence of steps in each cycle to remain the same, whilst the length of the steps is varied to vary the offset. Assuming a fixed step period, the two steering probe sections 130b will again move forwards in steps, alternating one after the other, but one of the sections moves at a higher velocity, and therefore a greater distance with each step, than the other. Therefore the net offset between the two steering sections increases at each step. Alternatively this can be achieved with fixed velocity and variable step period.

It should be understood that FIGS. 16a, 16b, 17a and 17b only show movement of the two steering sections of the probe. The two non-steering sections are moved as well. In this embodiment each of the two non-steering sections moves once for each step of each of the steering sections. The order of movement in each movement cycle is thus: steering section 1, non-steering section 1, non-steering section 2, steering section 2, non-steering section 1, non-steering section 2. Therefore each of the non-steering sections moves twice as many steps as each of the steering sections, and with steps of half the length. One of the steering sections is always the leading section, with the two non-steering sections being brought level with the 'new' leading section each time one of the steering sections is moved forwards, or brought up to a position behind the leading section if there is a high net offset between the two steering sections. This has been found to produce low levels of tissue damage. In a modification to this embodiment all four of the sections have steering inserts in them. The sequence of movements can be the same as that described above, but as four steering directions can be chosen the probe can be steering in three dimensions rather than just two.

Figure 18:
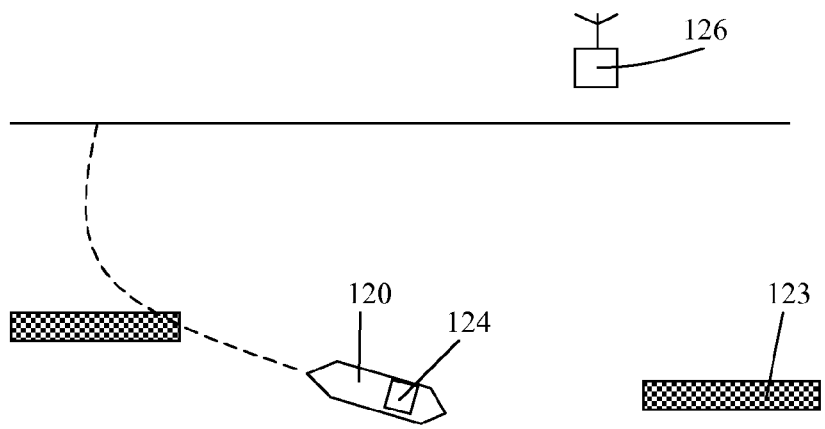
FIG. 18 is a diagram of a tethered search probe and control system according to a further embodiment of the invention.

Referring to FIG. 18, a probe according to a further embodiment of the invention is designed for underground exploration. The basic design is similar to that of FIG. 7, with the drive mechanism 184 being fully integrated into the probe body 180. However the scale of the probe in this case is of course significantly larger than those used for medical purposes. Also as the distances travelled by the probe might be large, the drive mechanism includes its own power supply. The controller of the drive mechanism 184 includes a transceiver arranged to communicate with a remote control unit 186 so that the probe can be controlled from the surface. The location of the probe can be determined using a suitable tracking device. The route of the probe can be planned and controlled, for example, so that it can collect samples from a number of target locations 183. Alternatively the route may not be planned, and the remote control unit 186 may include control inputs to enable a user to input steering commands which the remote control unit 186 is then arranged to communicate to the probe to control its route. In a further alternative embodiment the probe includes a detection system arranged to detect a signal from a target, such as an RF transmitter signal, a chemical tracer signal, or a heat sensor, and the controller of the drive system is arranged to determine a desired direction of movement from the detection system and to control the steering to achieve that direction of movement. Such arrangements can be used, for example, in search and rescue situations.

Figure 19:
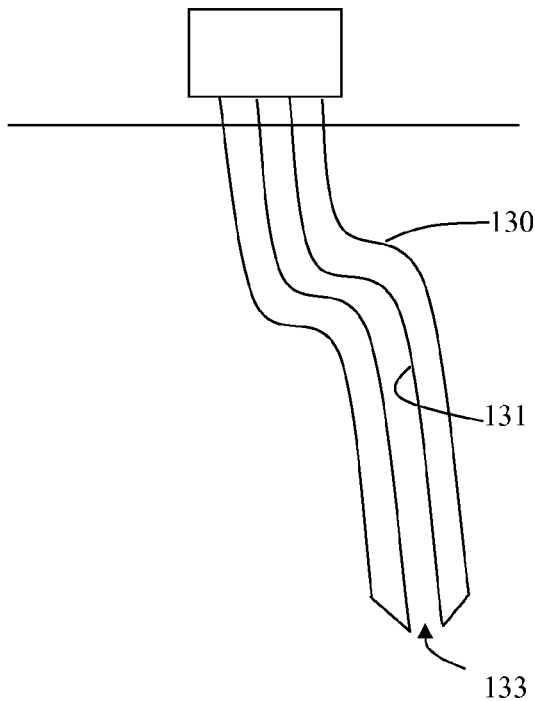
FIG. 19 is a schematic section through a probe according to a further embodiment of the invention.
Figure 19A:
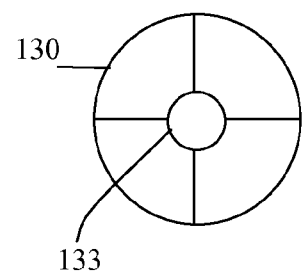
FIG. 19a is as cross section through the probe of FIG. 19.

Referring to FIGS. 19 and 19a, in a further embodiment of the invention, a probe for geological exploration is arranged to be driven from the surface, as in the surgical system of FIG. 4. However in this case the probe 190 has a central bore 191 extending along its longitudinal axis with an opening at the front end 193 of the probe. Therefore as the probe 190 moves into the ground, a core of sample material, such as soil, is collected in the central bore 191 which can then be extracted with the probe when the probe is moved back out of the ground. In general, provided the central bore 191 is empty on insertion of the probe, the material through which the probe is moving will collect in the bore 191 as the probe moves forwards. The core will also tend to be pulled out with the probe when the probe is extracted, but the probe may include closing mechanism to close the front end of the bore 191 before the probe is extracted to ensure that the core comes with it.

Another application for the probes like that of FIG. 19 is in search and rescue, particularly in snow, for example after an avalanche. In this application the location device in the probe is preferably arranged to transmit its position to a receiver on the surface, and the probe may include a heat sensor or other type of sensor to enable it to detect the presence of a person or animal in the snow.

The invention claimed is:

1. A steerable probe comprising: a body and a drive mechanism arranged to drive the probe through a sample, wherein the body comprises at least three body sections extending parallel to each other along the probe and each movable relative to the others along the probe, wherein at least two of the body sections are steering sections each of the steering sections being arranged to steer in a respective direction if the steering section is moved forwards of the other body sections, and the drive mechanism is configured to define a desired direction of steering along a curved path through the sample, is configured to move the body sections in a series of step cycles to drive the probe through the sample along the curved path, is configured to move each of the body sections at least one step in each cycle, and is configured to select one of the sections to move first in each cycle, the one of the sections being selected steering the probe in the desired direction along the curved path.

2. The probe according to claim 1 wherein the drive mechanism is arranged to apply a force in a forward direction to one of the body sections, and when applying said force in the forward direction to apply a force in a rearward direction to at least one of the other body sections.

3. The probe according to claim 2 wherein the drive mechanism is arranged to balance said forces so that it applies substantially zero net force to the probe.

4. The probe according to claim 1 wherein the drive mechanism is arranged to act between the body sections so as to apply forces that are internal to the probe.

5. The probe according to claim 1 wherein the steering section comprises a shaped tip.

6. The probe according to claim 1 wherein the steering section comprises resilient biasing means.

7. The probe according to claim 6 wherein the biasing means has a curvature that varies along its length so that, when said at least one body section is longitudinally offset from another of the body sections, it provides a steering curvature that varies with the longitudinal offset.

8. The probe according to claim 1 wherein the steering section comprises an active steering means arranged to provide a steering curvature that varies in response to a control input.

9. The probe according to claim 1 wherein at least one of the body sections is a non-steering section arranged to follow a path defined by the steering section.

10. The probe according to claim 1 wherein each of the body sections has an outer surface which forms part of an outer surface of the probe, the outer surface of the sections having a texture arranged to resist movement through the sample equally in both longitudinal directions of the probe.

11. The probe according to claim 1 wherein the drive mechanism comprises at least one actuator arranged to apply drive forces to the body sections and a controller arranged to control the at least one actuator so as to control movement of the probe.

12. The probe according to claim 11 wherein the at least one actuator is mounted on the probe body and arranged to move with the probe body through the sample.

13. The probe according to claim 1 wherein the distance moved by each of the body sections in each cycle is variable so that a net offset between the body sections can be varied.

14. The probe according to claim 1 wherein the distance moved by each of the body sections in each step is variable so that a net offset between the body sections can be varied.

15. The probe according to claim 1 having a channel extending along it at least one of the body sections.

16. A probe system comprising the probe according to claim 1 and locating means arranged to locate the probe as it moves though the sample, wherein the drive mechanism is arranged to receive location signals from the locating means so as to provide closed loop control of the position of the probe.

17. The probe system according to claim 16 wherein the locating means is arranged to measure the position and orientation of a part of the probe.

18. The probe system according to claim 17 wherein the drive mechanism is arranged to define a desired path of the probe and to determine a positional error and a directional error from the measured position and orientation and the desired path.

19. The probe according to claim 1 further comprising a detection system, wherein the drive mechanism is arranged to determine a desired direction from the detection system and to control the movement of the body sections so as to move the probe towards the desired direction.

20. The probe according to claim 1 wherein three of the sections are steering sections so the probe can be steered in a three dimensional path.

* * * * *